United States Patent
Skarmoutsou et al.

(10) Patent No.: US 10,786,916 B2
(45) Date of Patent: Sep. 29, 2020

(54) RAZOR CARTRIDGE WITH LUBRICATING STRIP

(71) Applicant: Bic Violex S.A., Anixi (GR)

(72) Inventors: Amalia Skarmoutsou, Glyfada (GR); Nikolaos Chatzigrigoriou, Attica (GR)

(73) Assignee: BIC VIOLEX S.A., Anoixi (GR)

(*) Notice: Subject to any disclaimer, the term of this patent is extended or adjusted under 35 U.S.C. 154(b) by 0 days.

(21) Appl. No.: 16/296,873

(22) Filed: Mar. 8, 2019

(65) Prior Publication Data

US 2019/0275688 A1 Sep. 12, 2019

(30) Foreign Application Priority Data

Mar. 9, 2018 (EP) ..................................... 18305254

(51) Int. Cl.
| | | |
|---|---|---|
| *A61Q 9/00* | (2006.01) | |
| *A61K 8/86* | (2006.01) | |
| *B26B 21/44* | (2006.01) | |
| *C10M 107/28* | (2006.01) | |
| *C10M 107/34* | (2006.01) | |
| *A61K 8/81* | (2006.01) | |
| *B26B 21/40* | (2006.01) | |
| *C10N 50/08* | (2006.01) | |

(52) U.S. Cl.
CPC .......... *B26B 21/443* (2013.01); *A61K 8/8117* (2013.01); *A61K 8/8164* (2013.01); *A61K 8/86* (2013.01); *A61Q 9/00* (2013.01); *C10M 107/28* (2013.01); *C10M 107/34* (2013.01); *B26B 21/4068* (2013.01); *C10M 2205/043* (2013.01); *C10M 2209/0806* (2013.01); *C10M 2209/1023* (2013.01); *C10M 2209/1045* (2013.01); *C10M 2217/0443* (2013.01); *C10M 2217/0453* (2013.01); *C10M 2229/025* (2013.01); *C10N 2050/08* (2013.01)

(58) Field of Classification Search
CPC .............. B26B 21/4068; B26B 21/443; C10M 107/28; C10M 107/34; C10M 2205/043; C10M 2209/0806; C10M 2209/1023; C10M 2209/1045; C10M 2217/0443; C10M 2217/0453; C10M 2229/025

See application file for complete search history.

(56) References Cited

U.S. PATENT DOCUMENTS

| | | | |
|---|---|---|---|
| 8,951,545 B2 | 2/2015 | Arps et al. | |
| 9,333,658 B2 | 5/2016 | Carneiro et al. | |
| 2002/0157256 A1* | 10/2002 | Barone | ................ B26B 21/443 30/41 |
| 2011/0197448 A1 | 8/2011 | Stephens et al. | |
| 2012/0087981 A1 | 4/2012 | Wang et al. | |
| 2015/0166746 A1 | 6/2015 | Brule et al. | |
| 2017/0216442 A1 | 8/2017 | Burgio et al. | |

FOREIGN PATENT DOCUMENTS

| | | | | |
|---|---|---|---|---|
| EP | 1 252 984 A2 | 10/2002 | | |
| WO | WO-2016054167 A1 * | 4/2016 | ............... | A61Q 9/04 |

OTHER PUBLICATIONS

Dobrovszky et al.(Polymer Bulletin Feb. 2016; 26 pages). (Year: 2016).*

European Search Report dated Sep. 4, 2018, in EP application No. 18 30 5253 (6 pages).

* cited by examiner

*Primary Examiner* — Ernst V Arnold
(74) *Attorney, Agent, or Firm* — Bookoff McAndrews, PLLC

(57) ABSTRACT

The disclosure deals with a lubricative skin engaging member with progressive release of lubricating polymer from a water-insoluble matrix containing thermoplastic elastomer compound and maleic anhydride copolymer and lubricating polymer in concentration less than 30%. The disclosure lies in the use of the maleic anhydride in grafted form on polyethylene and the incorporation of water-soluble lubricating polymer in concentration less than 30% in the thermoplastic elastomer compound, leading to a lubricative mixture, and to a skin engaging member, with increased homogeneity and water absorption ability that assist in the lubricating polymer release in a progressive and controllable manner.

11 Claims, No Drawings

RAZOR CARTRIDGE WITH LUBRICATING STRIP

CROSS REFERENCE TO RELATED APPLICATION(S)

This application claims priority to European Application No. EP18305254.7, filed Mar. 9, 2018, the entire content of which is incorporated herein by reference.

FIELD

The present disclosure relates to a shaving system of the wet shave type, more particularly to a shaving system with a skin engaging member utilizing an improved shaving aid composition.

BACKGROUND

Shaving glideness and comfort can be enhanced by affixing to a razor cartridge a skin engaging member, also known as a lubricating element typically in a strip form, which continuously releases a shaving aid, typically a lubricant, during the shaving process. Such a lubricating element generally includes a water-insoluble polymer matrix, and a water-soluble component, which leaches out lubricant during shaving to enhance shaving glideness and comfort. Usually, skin engaging members suffer from the disadvantage that they release lubricant in a non-progressive and non-controllable manner, particularly after the first three or four shaves where release rate of the lubricant may drop off.

WO2016054167A1 discloses the concept of an erodible composition, with a lubricating rubber, containing 40-80% lubricant (Polyethylene oxide, i.e. PEO) and 5-40% support polymers, which can be maleic anhydride copolymer and styrene copolymer.

EP1252984 discloses a lubricative composition containing PEO as lubricant in concentration 30-90% and a thermoplastic elastomer in concentration 10-70%. This composition aims to provide comfort and performance during shaving.

EP2536390 discloses an erodible composition including a block copolymer as structuring polymer combined with hydrophobic compounds (e.g. petrolatum, esters, triglycerides, waxes) in concentration more than 50%, aiming to a homogeneous distribution of the water-insoluble structuring polymer throughout the hydrophobic phase so as the final composition to improve wear properties and durability.

SUMMARY

The aim of this disclosure is to provide a lubricative skin engaging member formulation with progressive release of lubricating polymer from a water-insoluble matrix. The novel features of the disclosure include the use of maleic anhydride copolymers (MAH) and the incorporation of lubricating polymer in concentration of less than 30% in the water-insoluble matrix blend, leading to a lubricative mixture with increased homogeneity and water absorption ability, assisting in lubricating polymer release in a progressive, regular and controllable way.

DETAILED DESCRIPTION

Accordingly, the present disclosure concerns a razor cartridge including a skin engaging member, the skin engaging member comprising:

a water-insoluble matrix including: maleic anhydride copolymer and a thermoplastic elastomer compound at least one water-soluble lubricating polymer dispersed in the water-insoluble matrix.

According to the present disclosure, the maleic anhydride copolymer may be maleic anhydride copolymer and/or mixtures of maleic anhydride copolymers. In further embodiments, the disclosure also concerns a razor cartridge, wherein the water-soluble lubricating polymer is from 1 to less than 30%, preferably from 15 to less than 30%, more preferably 25 to 29%, by weight of the skin engaging member.

Further, the disclosure pertains to a razor cartridge, wherein the water-insoluble matrix is from 70.2 to 99%, preferably 70.2 to 85%, more preferably 71 to 75%, by weight of the skin engaging member.

In all aspects of the disclosure, the concentration of lubricating polymer is less than 30%.

In yet further embodiments, the disclosure also concerns a razor cartridge, wherein the water-soluble lubricating polymer is selected from the group consisting of polyethylene oxide, polyethylene glycol, and mixtures thereof. Suitable water-soluble lubricating polymer may be, for example, Polyox WSR Coagulant from DOW and/or ALKOX E300 from Meisei and/or PEO® from Sumitomo Seika Chemical.

When polyethylene oxide is present, its molecular weight ($M_w$) is between 1,000,000 and 9,000,000 g/mol. In some examples, the molecular weight may be between 4,000,000 and 8,000,000 g/mol and in other examples, between 5,000,000 and 7,000,000 g/mol. When present, the molecular weight of polyethylene glycol is between 300 and 9,000 g/mol, in some example, and between 4,000 and 7,500 g/mol in other examples.

The razor cartridge according to the disclosure may have a PEG/PEO weight ratio in the water-insoluble matrix is from 1:2.33 to 1:99, preferably from 1:5.5 to 1:49, more preferably from 1:9 to 1:32.

The razor cartridge disclosed may contain maleic anhydride copolymer in about 0.1 to 25%, preferably 3 to 8%, more preferably 4 to 7.5% by weight of the skin engaging member.

The razor cartridge presently described may contain thermoplastic elastomer compound in quantity ranging from about 45.2 to 98.1%, preferably 45.2 to 77%, more preferably 60 to 75% by weight of the skin engaging member.

In embodiments, the thermoplastic elastomer compound, is selected from the group consisting of poly(styrene-butadiene-styrene) (SBS), styrene ethylene butylene styrene block copolymer (SEBS), styrene-isoprene-styrene copolymer (SIS), styrene/ethylene-propylene copolymer (SEPS), thermoplastic urethane (TPU), thermoplastic vulcanizates (TPV), thermoplastic silicon vulcanizates (TPSiV), polyether-block-amide (PEBA), co-polyester elastomer (COPE), and mixtures thereof. The preferred thermoplastic elastomer compound is selected in the group consisting of poly(styrene-butadiene-styrene) (SBS), styrene ethylene butylene styrene block copolymer (SEBS) and their mixtures. Suitable thermoplastic elastomers may be found under the following brands, for example: ADG® range by Kraiburg, and/or Laprene® range by SO.F.TER GROUP, Onflex® range by PolyOne GLS.

The maleic anhydride copolymer may have a viscosity, at 230° C., between 85,000 and 1,000,000 cps.

Razor cartridges according to the disclosure may have the water-insoluble matrix and/or the water-soluble lubricating polymer further supplemented with a skin care agent selected from the group consisting of vitamins, botanical extracts, salts, humectants, fragrances, essential oils, silicon oils, organic oils, waxes, antioxidants, exfoliants, depilatory agents, surfactants, hair and skin conditioning agents, anti-bacterial agents, anti-microbial, anti-irritants, antiseptics, biocides, preservatives, skin cooling and soothing agents, moisturizing and hydrating agents, skin protectants, colorants, film formers, processing thickening agents from the list of silica, fume silica, $TiO_2$ particles, and combinations thereof.

Further, the disclosure provides a razor cartridge, wherein maleic anhydride copolymer is a polyolefin or polystyrene polymer and/or copolymer grafted with maleic anhydride, more specifically, a polyethylene polymer grafted with maleic anhydride, and/or mixtures of maleic anhydride copolymers.

In embodiments, described is a process for manufacturing a skin engaging member including at least a water-soluble lubricating polymer, a maleic anhydride copolymer and a thermoplastic elastomer compound, wherein the process includes extruding, injection-molding, laminating or compression-molding a solvent-free composition.

The present disclosure also relates to a hair removal method with the delivering of a lubricating polymer onto the skin comprising the steps of:
  Providing a device comprising a razor cartridge as disclosed herein,
  Activating the skin engaging member by exposure to water,
  Contacting the skin with the skin engaging member so as to release the lubricating polymer on the skin surface.

The device may be a hair removal device.

The disclosed formulation of the skin engaging member is activated with water and the water-soluble ingredients are progressively transferred on the surface of the skin engaging member. It has been shown that lubricating polymer(s) enrich the surface through water activation, and thus assist in glideness.

The hair removal device may be of the wet shave type including a blade member, a support structure defining an external skin engaging portion adjacent to the blade member, wherein the external skin engaging portion includes a skin engaging member according to the disclosure.

In embodiments, the skin engaging member protrudes above, or is at the same level or is below the level of the surface of the skin engaging portion.

The disclosure also relates to methods of manufacturing such hair removal devices, the methods comprising at least one of the steps of extruding, injection-molding, laminating or compression-molding a solvent-free composition, including at least a water-soluble lubricating polymer, a maleic anhydride copolymer and a thermoplastic elastomer compound, to form a skin engaging member and attaching the skin engaging member to the support structure adjacent to the blade member.

The present disclosure distinguishes compared to WO2016054167 in at least the relation with its manufacturing process. The present disclosure concerns a lubricative formulation of a skin engaging member deprived from solvents, which means a less complicated production process with fewer steps till the completion of the final product and with more eco-friendly profile. WO2016054167 refers to an anhydrous film that can be incorporated in an article (final product) after a series of steps: the lubricating polymer and the support polymers are dispersed in solvent so as to be homogeneously mixed and then the solvent should be removed to form the dried film. Subsequently, the dried film can be cut into an appropriate size and shape so as to be incorporated in the final article (e.g. can be grounded to produce granules or powder and then formed into an article by extrusion or injection).

On the contrary, the present disclosure includes a simple production process, where the lubricating polymer is blended with the thermoplastic elastomer compound and the maleic anhydride copolymer. The solid mixture can directly be injected to an article (e.g. on cap, on typical guard bar area or on extended guard bar member, on the surface of the retaining means and/or on any auxiliary means of a razor head such as skin adaptor, customizing tool, and/or on any other suitable part of the shaving head), for the development of a razor component or cartridge. In addition, the absence of solvents in the present disclosure results in an eco-friendly process compared to the process of WO2016054167, where the solvent is an essential ingredient and should be non-aqueous, preferably either an alcohol, ether or a hydrocarbon.

The term "skin engaging member" signifies a physical structure which engages skin for controlled lubrication and skin management functions during shaving and may be of any type including, but not limited to, one or more fin elements, elongated filaments or protrusions, or nubs, or any other texture such as logos, designs, graphics. The skin engaging element may be upstanding or curved, flexible or rigid, may have planar or non-planar surfaces, may be contiguous, non-contiguous, patterned with any functional or decorative patterns of any shape and form, or any combination thereof.

The attaching of the skin engaging member to the support structure adjacent to the blade member can be permanent and substantially immovable or movable. Alternatively, the attaching can be non-permanent, and the member can be replaced for any reason such as customization and/or to extend lifetime of the razor, while the attaching can be conducted by different engineering methods like snap fit or other, for example.

The solution provided according to the present disclosure is that the developed formulation presents a progressive, regular and controllable lubricating polymer release when exposed to water, due to improved homogeneity and the ability of maleic anhydride to absorb water assisting in lubricating polymer dissolution.

When a skin engaging member according to the present disclosure is manufactured through extrusion, injection, and/or lamination process, and more preferably through injection process, the skin engaging member presents a homogeneous distribution of water-soluble lubricating polymer in the water-insoluble matrix. Homogeneous distribution is attributed to maleic anhydride incorporation that assist mixing of PEO with thermoplastic elastomer compound. During shaving, the water-soluble lubricating polymer is dissolved and assist wet razor to glide against skin. Water is also absorbed by expansion of the maleic anhydride assisting thermoplastic elastomer. The expansion enables progressively water-soluble lubricating polymer to be dissolved and move towards the surface of the skin engaging member to enrich shaving surface with lubricant to assist glideness and shaving comfort.

Compared to simple lubrication elements (e.g. "lubra strips"), which are commonly used (e.g. U.S. Pat. No. 9,333,658), the lubricative composition of the skin engaging member of the disclosure differs regarding the lubricating polymer release rate and the soft contact feeling that the formulation according to the present disclosure induces to the skin.

The advantages of the disclosure compared to the common lubrication means include:

Improved final product properties, since thermoplastic elastomer compounds chemistry enable tuning of their properties.

Soft contact with the skin and the ability to develop a product that could follow skin contours.

Increased lubrication/glideness of razor products by adding an extra lubricating feature on razor head upon a skin engaging member.

Pleasant feeling due to soft contact as showed in uses of present formulation in existing hair removal products.

The advantages of the present disclosure result from the combination of the lubricating polymer with the maleic anhydride copolymer, where the lubricating polymer is involved in concentration less than 30%.

The presence of the lubricating polymer in the formulation of the skin engaging member, according to the disclosure, in concentration less than 30% results in a pleasant aesthetics appearance of lubricative skin engaging member after 10 uses. The concentration of less than 30% of lubricating water-soluble components is homogeneously distributed in the thermoplastic elastomer compound with incorporated maleic anhydride copolymer, assisting progressive lubricating components release for a longer period. Compared to state-of-the-art formulations of lubricative strips with poor durability exhibiting deformations (e.g. craters) and/or surface alterations, and/or discoloration, the corresponding lubricative skin engaging member according to the formulation of the disclosure does not show any deformations or alterations or discolorations. Evidence of the durability of the present lubricative skin engaging member formulation comes as a result from tests conducted on users indicating ~16% reduction of fluidity within a 10 days test and no profound destruction of the lubricative skin engaging member formulation of the disclosure.

Maleic anhydride compounds are used in different application in plastics technologies. Maleic anhydride copolymers and/or mixtures are incorporated in thermoplastic elastomer compounds to improve mixing; more specifically, the incorporation of a polyethylene grafted with maleic anhydride in SEBS thermoplastic elastomer compounds, assists thermoplastic elastomer compound homogeneity, considering that SEBS thermoplastic elastomers are mostly compounded with polyethylene, polypropylene and polyolefin elastomer. An alternative function of maleic anhydride copolymers incorporation in thermoplastic elastomer compounds is adhesion enhancement on thermoplastic substrates, such as polycarbonate, polyamide, Acrylonitrile Butadiene Styrene (ABS), from which the plastic components of the razor (e.g. guard, skin adaptor) are prepared.

The disclosed formulation achieved the homogeneous distribution of lubricative water-soluble polymer and/or mixtures in a water-insoluble matrix comprised of a thermoplastic elastomer and/or thermoplastic urethane compounds and/or mixtures, and a maleic anhydride copolymer, and/or mixtures.

Consequently, the lubricative skin engaging member component according to the disclosure is more durable and safely attached onto the razor. The lubricative skin engaging member progressively releases the lubricating polymer, due to water uptake ability of maleic anhydride copolymer that assists in thermoplastic elastomer compound chains expansion and the subsequent progressive release and dissolution of the water-soluble lubricating polymer, allowing a larger number of shaving uses.

The aim of the present disclosure is to provide a lubricative skin engaging member with progressive release of lubricating polymer from a blend containing a water-insoluble matrix comprising thermoplastic elastomer compound and maleic anhydride copolymer, and at least one water-soluble lubricating polymer in concentration less than 30%. The novel features of the disclosure are the use of the maleic anhydride in grafted form on polymer, and more preferably on polyethylene and the incorporation of lubricating polymers in concentration less than 30% in the thermoplastic elastomer compound, leading to a lubricative mixture, and to a skin engaging member, with increased homogeneity and water absorption ability that assist in lubricating polymer release in a progressive and controllable way.

The skin engaging member according to the disclosure leads to a homogeneous mixture due to the grafted maleic anhydride on polyethylene (PE-g-MAH) without additives and/or solvents. The lubricative composition of the skin engaging member of the disclosure presents a homogeneous distribution of water-soluble and water-insoluble ingredients and has increased water uptake to assist lubricating polymer release, whereas the WO2016054167 mentions that the support polymer is wearing out along with PEO release from the structure and the number of uses is controlled by the thickness of the film. In other words, in terms of performance for WO2016054167, more repeated uses are achieved with thicker films, whereas in the case of the present disclosure there is no evidence of thickness change. Also, the maleic anhydride compound of WO2016054167 is mentioned as polymethyl vinyl ether/maleic anhydride copolymer, whereas the present disclosure refers to a polyethylene compound grafted with maleic anhydride.

The invention claimed is:

1. A skin engaging member for a razor cartridge comprising:
   a water-insoluble matrix including: a maleic anhydride copolymer in grafted form and a thermoplastic elastomer compound; and
   a water-soluble lubricating polymer dispersed in the water-insoluble matrix,
   wherein the water-soluble lubricating polymer is in a concentration of less than 30% by weight of the skin engaging member, and wherein there is no evidence of thickness change in the skin engaging member after repeated uses.

2. The skin engaging member according to claim 1, wherein the water-soluble lubricating polymer is from 1 to less than 30% by weight of the skin engaging member.

3. The skin engaging member according to claim 1, wherein the water-insoluble matrix is from 70.2 to 99%, by weight of the skin engaging member.

4. The skin engaging member according to claim 1, wherein the water-soluble lubricating polymer is selected from the group consisting of polyethylene oxide (PEO), polyethylene glycol (PEG), and mixtures thereof.

5. The skin engaging member according to claim 4, wherein a PEG/PEO weight ratio in the water-insoluble matrix is from 1:2.33 to 1:99.

6. The skin engaging member according to claim 1, wherein the maleic anhydride copolymer is 0.1 to 25% by weight of the skin engaging member.

7. The skin engaging member according to claim 1, wherein the thermoplastic elastomer compound is from 45.2 to 98.1% by weight of the skin engaging member.

8. The skin engaging member according to claim 1, wherein the thermoplastic elastomer compound, is selected from the group consisting of poly(styrene-butadiene-styrene) (SBS), styrene ethylene butylene styrene block copolymer (SEBS), styrene-isoprene-styrene copolymer (SIS), styrene/ethylene-propylene copolymer (SEPS), thermoplastic urethane (TPU), thermoplastic vulcanizates (TPV), thermoplastic silicon vulcanizates (TPSiV), poly-ether-block-amide (PEBA), co-polyester elastomer (COPE), and mixtures thereof.

9. The skin engaging member according to claim 1, wherein the water-insoluble matrix and/or the water-soluble lubricating polymer further comprises a skin care agent selected from the group consisting of vitamins, botanical extracts, salts, humectants, fragrances, essential oils, silicon oils, organic oils, waxes, antioxidants, exfoliants, depilatory agents, surfactants, hair and skin conditioning agents, anti-bacterial agents, anti-microbial, anti-irritants, antiseptics, biocides, preservatives, skin cooling and soothing agents, moisturizing and hydrating agents, skin protectants, colorants, film formers, processing thickening agents from the list of silica, fume silica, $TiO_2$ particles, and combinations thereof.

10. The skin engaging member according to claim 1, wherein the maleic anhydride copolymer is a polyolefin or polystyrene polymer grafted with maleic anhydride.

11. The skin engaging member according to claim 1, wherein the maleic anhydride copolymer is a polyethylene polymer grafted with maleic anhydride.

* * * * *